US010429182B2

(12) United States Patent
Uhde et al.

(10) Patent No.: US 10,429,182 B2
(45) Date of Patent: Oct. 1, 2019

(54) METHOD AND APPARATUS FOR DETECTING UNDESIRABLE ROTATION OF MEDICAL MARKERS

(75) Inventors: Jorg Uhde, Munich (DE); Robert Essenreiter, Munich (DE)

(73) Assignee: Brainlab AG, Munich (DE)

( * ) Notice: Subject to any disclaimer, the term of this patent is extended or adjusted under 35 U.S.C. 154(b) by 284 days.

(21) Appl. No.: 14/408,984

(22) PCT Filed: Jun. 19, 2012

(86) PCT No.: PCT/EP2012/061678
§ 371 (c)(1),
(2), (4) Date: Dec. 18, 2014

(87) PCT Pub. No.: WO2013/189520
PCT Pub. Date: Dec. 27, 2013

(65) Prior Publication Data
US 2015/0338214 A1     Nov. 26, 2015

(51) Int. Cl.
*A61B 34/20* (2016.01)
*A61B 90/00* (2016.01)
(Continued)

(52) U.S. Cl.
CPC ............. *G01B 21/22* (2013.01); *A61B 34/20* (2016.02); *A61B 90/39* (2016.02); *G16H 20/40* (2018.01); *A61B 2034/2055* (2016.02); *A61B 2090/0812* (2016.02); *A61B 2090/3983* (2016.02); *G06F 17/40* (2013.01); *G06F 19/00* (2013.01)

(58) Field of Classification Search
None
See application file for complete search history.

(56) References Cited

U.S. PATENT DOCUMENTS 3,518,368 A * 6/1970 Olson ................ G01S 3/7864
                                                 235/411
4,099,880 A * 7/1978 Kano ..................... G01C 11/14
                                                     356/2
(Continued)

OTHER PUBLICATIONS

International Search Report and Written Opinion for International Application No. PCT/EP2012/061678 dated Mar. 15, 2013.

*Primary Examiner* — Alexander Satanovsky
*Assistant Examiner* — Brent A. Fairbanks
(74) *Attorney, Agent, or Firm* — Tucker Ellis LLP

(57) ABSTRACT

Provided is a data processing method for determining rotation by a marker device of a medical tracking system about its mount. The data processing method includes acquiring a first marker device position dataset which represents a position of the marker device before a movement of the marker device. A second marker device position dataset is acquired which represents the position of the marker device after a movement of the marker device. A marker device displacement dataset is calculated, which represents the displacement of the marker device, from the first and second marker device position datasets. At least one axis of rotation of the marker device displacement dataset is calculated. A determination is made whether or not the marker device is rotated about its mount from the position of the at least one axis of rotation relative to the marker device.

20 Claims, 7 Drawing Sheets

(51) Int. Cl.
  *G01B 21/22* (2006.01)
  *G06F 17/40* (2006.01)
  *G16H 20/40* (2018.01)
  *G06F 19/00* (2018.01)

(56) References Cited

U.S. PATENT DOCUMENTS

| | | | | |
|---|---|---|---|---|
| 6,125,197 A | * | 9/2000 | Mack | H04N 13/0221 |
| | | | | 256/12 |
| 6,877,239 B2 | * | 4/2005 | Leitner | G01S 5/163 |
| | | | | 33/511 |
| 7,257,237 B1 | * | 8/2007 | Luck | A61B 5/1113 |
| | | | | 382/103 |
| 8,126,535 B2 | * | 2/2012 | Maier | G06F 19/3437 |
| | | | | 600/424 |
| 8,469,965 B2 | * | 6/2013 | Neubauer et al. | A61B 34/20 |
| | | | | 600/429 |
| 8,918,210 B2 | * | 12/2014 | Kagawa | B25J 9/1692 |
| | | | | 318/568.11 |
| 8,988,505 B2 | * | 3/2015 | Schaerer | A61B 19/5244 |
| | | | | 348/46 |
| 9,410,791 B2 | * | 8/2016 | Ely | G01D 5/2013 |
| 2003/0056385 A1 | | 3/2003 | Leitner et al. | |
| 2003/0105470 A1 | | 6/2003 | White | |
| 2004/0013414 A1 | * | 1/2004 | Karger | A61N 5/1049 |
| | | | | 386/224 |
| 2005/0267358 A1 | | 12/2005 | Tuma et al. | |
| 2007/0049819 A1 | * | 3/2007 | Stifter | A61B 34/20 |
| | | | | 600/426 |
| 2008/0154125 A1 | * | 6/2008 | Maier | A61B 90/36 |
| | | | | 600/424 |
| 2009/0099445 A1 | * | 4/2009 | Burger | A61B 34/20 |
| | | | | 600/424 |
| 2009/0247861 A1 | * | 10/2009 | Manus | A61B 90/36 |
| | | | | 600/424 |
| 2010/0286508 A1 | * | 11/2010 | Neubauer et al. | A61B 34/20 |
| | | | | 600/426 |
| 2011/0254922 A1 | * | 10/2011 | Schaerer | A61B 19/5244 |
| | | | | 348/46 |
| 2012/0239194 A1 | * | 9/2012 | Kagawa | B25J 9/1692 |
| | | | | 700/254 |
| 2013/0257417 A1 | * | 10/2013 | Ely | G01B 7/30 |
| | | | | 324/207.22 |
| 2013/0345718 A1 | * | 12/2013 | Crawford | A61B 17/025 |
| | | | | 606/130 |
| 2016/0242849 A9 | * | 8/2016 | Crawford | A61B 17/025 |

* cited by examiner

METHOD AND APPARATUS FOR DETECTING UNDESIRABLE ROTATION OF MEDICAL MARKERS

RELATED APPLICATION DATA

This application is a national phase application of International Application No. PCT/EP2012/061678 filed Jun. 19, 2012 and published in the English language.

BACKGROUND

The present invention relates to a data processing method for determining rotation of a marker device of a medical tracking system about its mount, and to a computer program which implements the method on a computer on which the program is running.

In recent years, it has become quite common to use medical tracking systems to track objects such as medical instruments or (parts of) a patient, for example during surgery. A marker device comprising one or more markers is attached to the object in a fixed manner using a mount. When the position of the marker device is tracked, for example using a stereoscopic camera, the rigid connection between the object and the marker device means that the position of the object can also be tracked. However, the connection between the object and the marker device need not be fixed: the mount can for example comprise lockable axes of rotation, also referred to as mechanical axes, in order to initially adjust the position of a marker device relative to the object. This can be advantageous in obtaining a relative position which does not disrupt surgery. In another example, the mount itself can be pivoted relative to the object, for example if the mount is attached to the object using a screw. During the tracking process, the rotation of the marker device about one of the aforementioned axes is undesirable, because it destroys the fixed (and preferably registered) relative position between the marker device and the object.

It is therefore an object of the present invention to determine whether or not an (undesirable and unintentional) rotation by the marker device about its mount has occurred. In particular, the intention is to determine whether or not a movement of a marker device is caused by a rotation about its mount. This information can be used to issue a warning based on warning information, in order to inform the user of the tracking system accordingly.

In this document, the term "mount" not only means the clamp or holder between the object and the marker device but also the fixation of the clamp or holder to the object. A rotation about the mount also encompasses a rotation about a part of the mount.

This problem is solved by the subject-matter of any of the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically sensible and feasible. In particular, a feature of one embodiment which has the same or a similar function as another feature of another embodiment can be exchanged. In particular, a feature of one embodiment which provides an additional function to another embodiment can be added to said other embodiment.

The present invention relates to a data processing method for determining a rotation by a marker device of a medical tracking system about its mount. By means of the mount, the marker device is attached to an object such as a medical instrument or a (part of) a body, such as for example a bone. The present invention therefore also relates to determining a rotation by the marker device relative to an object which it is attached to.

It is the function of a marker to be detected by a marker detection device (for example, a camera or an ultrasound receiver or analytical devices such as a CT or MRI), such that its spatial position (i.e. its spatial location and/or alignment) can be ascertained. The detection device is in particular part of a tracking system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or a marker or a plurality of (individual) markers which are preferably in a predetermined spatial relationship. A marker device comprises one, two, three or more markers, wherein said two or more markers are in a predetermined spatial relationship. This predetermined spatial relationship is in particular known to a tracking system and for example stored in a computer of the tracking system.

A tracking system, in particular a surgical tracking system, is understood to mean a system which can comprise: at least one marker device; a transmitter which emits electromagnetic waves and/or radiation and/or ultrasound waves; a receiver (or marker detection device) which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example, a visual indicating device such as a monitor and/or an audio indicating device such as a loudspeaker and/or a tactile indicating device such as a vibrator) and advantageously a permanent data memory, wherein the data processing device processes tracking data forwarded to it by the receiver and can advantageously output guidance information to a user via the indicating device. The tracking data can be stored in the permanent data memory and for example compared with data stored in said memory beforehand.

One step of the method involves acquiring a first marker device position dataset which represents the (first) position of the marker device before a movement of the marker device. Another step involves acquiring a second marker device position dataset which represents the (second) position of the marker device after a movement of the marker device. The movement of the marker device can be any kind of movement, i.e. an intentional movement such as a movement caused by moving the object which the marker device is attached to, an unintentional rotation of the marker device about its mount, or a combination of these.

Preferably, a position of the marker device is specified in a co-ordinate system which is defined relative to the receiver of the tracking system.

Preferably, the positions of the marker device represented by the first and second marker device position datasets are static, such that the movement relates to a terminated change in the position of the marker device. In this approach, a determination as to whether or not an undesirable rotation has occurred is not made while the marker device is in motion. However, it is also possible for the marker device to not be static, i.e. to be in motion, while one or both of the marker device position datasets are acquired.

A subsequent step of the method involves calculating a marker device displacement dataset which represents the displacement of the marker device. The marker device displacement dataset is calculated from the first and second marker device position datasets. It describes the displacement of the marker device between the first position before the movement and the second position after the movement. It should be noted that "position" here means a spatial location in up to three translational dimensions, a rotational alignment in up to three rotational dimensions or preferably a combination of these. The displacement therefore describes a change in the location in up to three translational dimensions, a change in the rotational alignment in up to three rotational dimensions or a combination of these.

Another step of the method involves calculating at least one axis of rotation of the marker device displacement dataset. An axis of rotation is an axis about which a rotation in one rotational dimension is defined. An axis of rotation is defined by its position, or at least by the position of one point lying on the axis of rotation, and its orientation or alignment in space. Calculating an axis of rotation therefore means calculating a value which describes a position of the axis of rotation.

Another step of the method involves determining whether or not the marker device is rotated about its mount from the position of the at least one axis of rotation relative to the marker device. The inventors have found that some positions of an axis of rotation relative to the marker device are characteristic of a rotation of the marker device about its mount rather than an intentional movement of the marker device. In one embodiment, the marker device is determined to have rotated about its mount if the distance between an axis of rotation and a point defined relative to the marker device is below a predetermined maximum distance threshold. This defined point is also referred to as the reference point of the marker device. In other words, the criterion applied is the proximity of the axis of rotation to the marker device. The point to which the distance is calculated is defined in accordance with the geometry of the marker device, i.e. this point is for example the central point of the markers constituting the marker device. Alternatively, the point lies in a mechanical axis of the mount, preferably the mechanical axis closest to the marker device.

The maximum distance threshold defines the maximum distance between the axis of rotation and the defined point at which the marker device is still determined to have rotated about its mount. The maximum distance threshold can for example depend on the size of the marker device, the type of mount, the medical application in which the method is employed or any combination of these.

The method optionally also comprises the steps of acquiring a mechanical axis indication information dataset which represents information on the position of a mechanical axis of the mount and adjusting the maximum distance threshold in accordance with the mechanical indication information dataset. The maximum distance threshold is calculated so as to include the mechanical axis. Preferably, the maximum distance threshold is calculated to be 2%, 5%, 10%, 20% or 25% larger than the distance between the reference point of the marker device and the mechanical axis. A tracked pointer is for example used to acquire one or more points of a mechanical axis of the mount. This information can be used to define the mechanical axis relative to the marker device.

In another embodiment, the marker device is determined to have rotated about its mount if the difference between a determined axis of rotation and a mechanical axis of the mount is below a predetermined axis deviation threshold. The axis deviation threshold relates to the distance between an axis of rotation and a mechanical axis, the angle between an axis of rotation and the mechanical axis or a combination of these. If an axis of rotation coincides with a mechanical axis, allowing a deviation as defined by the axis deviation threshold, then the displacement of the marker device is determined to be at least partly caused by a rotation of the marker device about its mount.

In a preferred embodiment, the marker device position datasets are marker device position matrices, and the marker device displacement dataset is a marker device displacement matrix. The matrices preferably have the same size and are quadratic. The matrices are in particular 4×4 matrices. In each marker device position matrix, and preferably also in the marker device displacement matrix, the spatial location and rotational alignment of the marker device are coded into the entries of the matrix in accordance with a predetermined rule. Preferably, the known approach of coding three-dimensional positions (or translations) and three-dimensional alignments (or rotations) into a transformation matrix using homogeneous coordinates in a 4D space is applied. The position of a marker device is preferably determined relative to a reference coordinate system, such as a coordinate system associated with a medical navigation system which is used to acquire the position of the marker device. The rotations are defined about the axes of this coordinate system.

In one embodiment, the method comprises the additional step of calculating the Euler angles of a marker device displacement matrix and performing the step of determining the at least one axis of rotation and all subsequent steps only if at least one of the Euler angles is larger than a predetermined minimum angle threshold. The minimum angle threshold is set for example to 0.5°, 1°, 2°, 3° or 5°. Requiring a minimum rotation prevents false positives, which indicate that the marker device is rotated about its mount when this is not actually the case, in an environment in which noise is present in the detection of the position of the marker device.

In a preferred embodiment, the at least one axis of rotation is calculated as an eigenvector of the marker device displacement matrix. An eigenvector of a matrix is a vector which, when multiplied by the matrix, does not change its direction. This means that multiplying the eigenvector by the marker device displacement matrix does not change the direction of the eigenvector. This in turn means that the eigenvector must coincide with an axis of rotation in the marker device displacement matrix.

Preferably, only eigenspaces with two dimensions are further investigated. This means that there are two identical real eigenvalues and two eigenvectors. Due to the usage of homogeneous coordinates in four dimensions, the last component of one of these eigenvectors is equal to zero. This eigenvector is interpreted as the direction of the axis of rotation, while the other eigenvector defines a point on the axis of rotation.

If none of the eigenvectors has a last component equal to zero, then the eigenvectors can be transformed, for example using Gaussian elimination. This results in one of the eigenvectors having a last component equal to zero.

Preferably, only one axis of rotation corresponding to the eigenvector with the largest eigenvalue is determined. This reduces the computational complexity by reducing the analysis to one axis of rotation, namely the axis of the largest rotation angle.

In a preferred embodiment, the marker device displacement matrix is calculated as the product of the inverse of the second marker device position matrix and the first marker device position matrix.

As outlined above, it is advantageous if the position of the marker device before and after the movement is static. This is ensured by an embodiment in which a marker device position dataset is acquired by acquiring a plurality of sample marker device position datasets, averaging the plurality of sample marker device position datasets and using the average as the marker device position dataset if the standard deviation of the sample marker device position datasets is below a predetermined position threshold. The averaging process eliminates the noise which occurs when ascertaining the position of the marker device using the receiver of the tracking system. If the standard deviation of the sample marker device position datasets is above the predetermined position threshold, then this is interpreted to mean that the marker device was in motion while the plurality of sample marker position datasets were acquired. In this embodiment, the position of the marker device as a whole is averaged.

In an alternative embodiment, a marker device position dataset is acquired by sampling, for each marker of the marker device, a plurality of sample marker position datasets which each represent the position of the respective marker, averaging the plurality of sample marker position datasets and using the average as a marker position in the marker device position dataset if the standard deviation of the sample marker position datasets for each marker is below a predetermined position threshold. This embodiment is similar to the previous embodiment, but instead of averaging the position of the marker device as a whole, the positions of the respective markers of the marker device are averaged.

In each of the last two embodiments, a plurality of sample datasets (sample marker device position datasets or sample marker position datasets) are acquired. Preferably, the sample datasets are acquired consecutively over time. The sample datasets can be averaged in blocks or by a sliding window protocol. In the block approach, a number of sample datasets are acquired, averaged and analysed in terms of their standard deviation. Once this plurality of sample datasets have been analysed, they are all discarded and a new block of sample datasets are acquired and analysed. In the sliding window approach, the oldest sample dataset is discarded and a new sample dataset is acquired. This means that the oldest sample dataset is always replaced by a new sample dataset, and the analysis is performed on a number of the latest sample datasets.

Preferably, the marker device displacement dataset is calculated from the averaged first and second marker device position datasets obtained as described above.

In an alternative embodiment, a plurality of sample second marker device position datasets are acquired. A plurality of sample marker device displacement datasets are calculated which each represent the displacement of the marker device between the first marker device position dataset and a corresponding sample second marker device position dataset of the plurality of sample second marker device position datasets. Preferably, the first marker device position dataset is an averaged dataset as described in the previous embodiments. The plurality of sample marker device displacement datasets are averaged, and the average is used as the marker device displacement dataset if the standard deviation of the plurality of sample marker device displacement datasets is below a predetermined displacement threshold. This implies that the second position of the marker device is static.

In this embodiment, the marker device displacement dataset is not calculated from the (averaged) first and second marker device position datasets; instead, a plurality of sample marker device displacement datasets are calculated for a plurality of sample second marker device position datasets, and the plurality of sample marker device displacement datasets are then averaged. By analogy with the previous embodiments, the displacement threshold is used to determine whether or not the marker device was in motion while the sample second marker device position datasets were acquired. As described above, the average can be calculated in blocks or by a sliding window protocol.

Another embodiment relates to the presence of two different marker devices. Marker device displacement datasets are calculated for the two different marker devices. At least one axis of rotation is calculated for each marker device. This is performed as described above for a single marker device. The marker devices are determined to have not rotated about their respective mounts if each axis of rotation of the first marker device has a corresponding axis of rotation of the second marker device at a distance which is below a predetermined axis divergence threshold. In other words, this embodiment relates to comparing the axes of rotation of the two marker devices. If the axes of rotation of the two marker devices do coincide in pairs within a certain allowed divergence described by the axis divergence threshold, then this is interpreted to the effect that the two marker devices have performed the same movement and neither of the marker devices has rotated about its respective mount.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2). A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

FIGURES

The invention shall now be described in more detail with reference to the accompanying figures, which show:

DETAILED DESCRIPTION

Figures 1A, 1B:
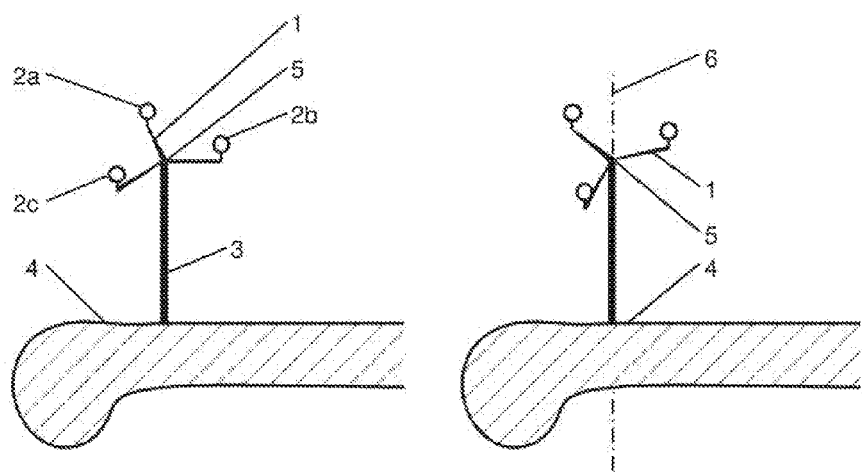
FIGS. 1a and 1b illustrate a marker device in two different rotational positions.

FIGS. 1a and 1b show a marker device 1 attached to an object 4, such as a bone, via a mount 3 in two different rotational positions. The marker device 1 comprises three marker spheres 2a, 2b and 2c. A (virtual or imaginary) point 5 is defined as the central point of the marker device 1 and also referred to as the reference point. In this example, the mount 3 is attached to the bone 4 via a single screw in order to reduce the burden on the bone 4. However, this has the disadvantage that the mount 3 can rotate relative to the screw, and therefore the bone 4, about its longitudinal axis. In FIG. 1a, the longitudinal axis of the mount 3 is vertical. In FIG. 1b, the marker device is rotated by 90 degrees about the longitudinal axis of the mount 3 as compared to FIG. 1a.

Figure 4:
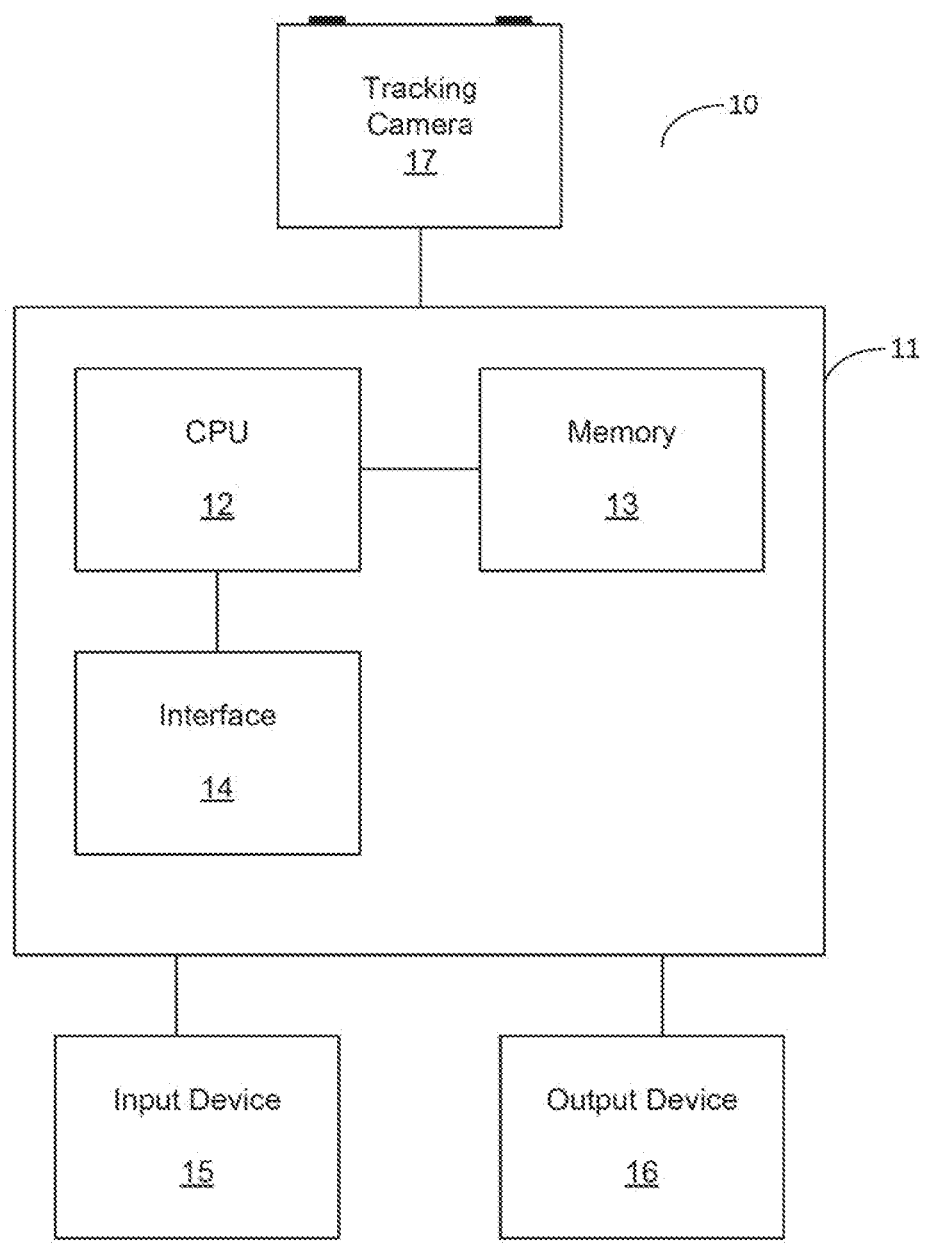
FIG. 4 illustrates a computer for carrying out the invention.

FIG. 4 shows a medical tracking system 10 comprising a computer 11 which is connected to a stereoscopic tracking camera 17 as an example of a marker detection device. The computer 11 comprises a central processing unit (CPU) 12 which is connected to a memory 13 and an interface 14. The computer 11 can be connected to a network or another apparatus via the interface 14. The memory 13 stores instructions which are performed by the CPU 12 and data which are to be processed by the CPU 12. The computer 11 is connected to an input device 15, such as a mouse or a keyboard, and an output device 16 such as a display or a speaker.

The tracking camera 17 is adapted to capture a stereoscopic image of at least the marker device 1. The position of the marker spheres 2a to 2c can be ascertained in this stereoscopic image. The position, i.e. the spatial location and the rotational alignment, of the marker device 1 can be calculated from the spatial locations of the markers 2a to 2c. A location, rotation or position is preferably defined in a co-ordinate system of the tracking camera 17. The stereoscopic image can be analysed in the stereoscopic camera 17, in the computer 11 or in both in combination in order to obtain the locations of the markers 2a to 2c or the positions of the marker device 1.

In a first step, the CPU 12 uses the tracking camera 17 to acquire a first marker device position dataset which represents the position of the marker device 1 in a first position shown in FIG. 1a. The mount 3 and therefore also the marker device 1 is then unintentionally rotated about the longitudinal axis of the mount 3 into a second position shown in FIG. 1b. The CPU 12 then uses the tracking camera 17 to acquire a second marker device position dataset which represents the position of the marker device 1 in the second position shown in FIG. 1b.

In the present embodiment, the marker device position datasets are 4×4 matrices in which three rotational degrees of freedom and three translational degrees of freedom are coded. In the present example, the first marker device position matrix P1 is given as $$P1 = \begin{pmatrix} 1 & 0 & 0 & 0 \\ 0 & 1 & 0 & 0 \\ 0 & 0 & 1 & 100 \\ 0 & 0 & 0 & 1 \end{pmatrix}$$

and the second marker device position matrix P2 is found to be $$P2 = \begin{pmatrix} 0 & 0 & -1 & -100 \\ 0 & 1 & 0 & 0 \\ 1 & 0 & 0 & 100 \\ 0 & 0 & 0 & 1 \end{pmatrix}.$$

The matrices P1 and P2 are stored in the memory 13. The CPU then calculates a marker device displacement matrix DM as $$DM = inv(P2) * P1 =$$

$$\begin{pmatrix} 0 & 0 & 1 & 0 \\ 0 & 1 & 0 & 0 \\ -1 & 0 & 0 & -100 \\ 0 & 0 & 0 & 1 \end{pmatrix} * \begin{pmatrix} 1 & 0 & 0 & 0 \\ 0 & 1 & 0 & 0 \\ 0 & 0 & 1 & 100 \\ 0 & 0 & 0 & 1 \end{pmatrix} = \begin{pmatrix} 0 & 0 & 1 & 100 \\ 0 & 1 & 0 & 0 \\ -1 & 0 & 0 & -100 \\ 0 & 0 & 0 & 1 \end{pmatrix}.$$

From this matrix DM, the CPU 12 calculates the Euler angles as $\varphi=180°$, $\theta=90°$ and $\psi=0°$. The Euler angles are then compared with a minimum angle threshold, which in the present example is 2 degrees. Since at least one of the Euler angles is above this threshold, it is determined that the marker device 1 has been rotated. At this time, the CPU 12 has not yet calculated whether this rotation was intentional or not.

The CPU 12 then calculates an eigenvector of the marker device displacement matrix DM, resulting in the vector $$v_{rot} = \begin{pmatrix} 0 \\ 1 \\ 0 \\ 0 \end{pmatrix}$$

through the point $P_{rot}=(0, 0, -100, 1)$.

The eigenvector $v_{rot}$ is interpreted as defining an axis of rotation about which the marker device 1 has been rotated, the axis of rotation running through the point $P_{rot}$. The CPU 12 then determines the distance between the central point 5 of the marker device 1 and the calculated axis of rotation 6 and compares this distance with a maximum distance threshold, such as for example 50 cm. In the present example, the axis of rotation 6 runs exactly through the central point 5, such that the distance is 0 cm. The distance is therefore below the maximum distance threshold, such that the CPU 12 concludes that the rotation of the marker device 1 was an unintentional rotation about its mount 3 and was not caused by a rotation of the bone 4.

Preferably, the central processing unit 12 calculates indication information which is then provided to the output device 16. The indication information indicates that the CPU 12 has determined that the marker device 1 has rotated about its mount 3, which means that the rotation of the marker device 1 was unintentional. The indication information can be optical and/or acoustic and/or tactile in nature.

Determining whether or not a movement of the marker device 1 was intentional is advantageously suspended while the marker device 1 is in motion. In other words, the first and second marker device positions should be static. The CPU 12 therefore does not merely acquire a single first marker device position matrix and a single second marker device position matrix, but rather a plurality of sample marker device position matrices, such as for example 10 sample marker device position matrices, for each position and performs an averaging process on the plurality of sample marker device position matrices for each position. The standard deviation of the sample marker device position matrices from the calculated average is then calculated and compared with a position threshold. If the standard deviation is below the position threshold, then the CPU 12 concludes that the position of the marker device 1 is static over the plurality of sample marker device position matrices. Since acquiring a marker device position matrix is influenced by noise and other inaccuracies, the sample marker device position matrices are not necessarily identical even if they represent the same marker device position. This issue is overcome by comparing the average with a position threshold.

Figure 2:
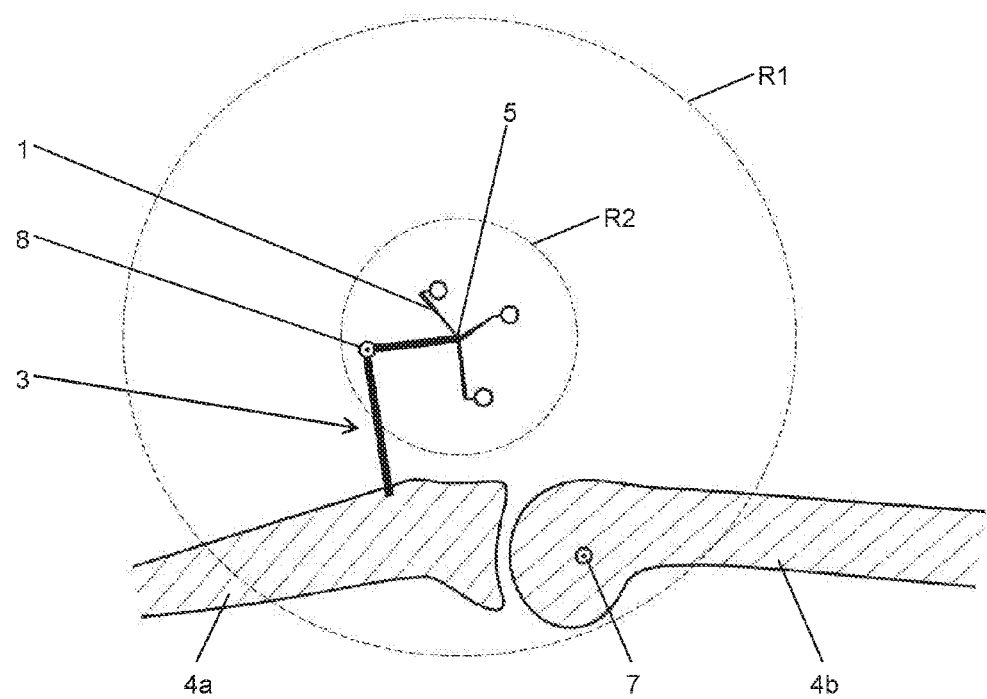
FIG. 2 illustrates the adaptation of a maximum distance threshold.

FIG. 2 shows an example of a configuration in which it is advantageous to adjust the maximum distance threshold. In the arrangement shown, two bones 4a and 4b form a joint, such as for example the tibia and femur forming a knee joint. The joint can perform a rotation about the joint axis 7. The marker device 1 comprising the central point 5 is connected to one 4a of the bones via a mount 3. The mount 3 consists of two parts which are connected via a hinge 8 which is a mechanical axis of the mount 3. The two concentric circles R1 and R2 centred about the central point 5 indicate two different maximum distance thresholds. The radius of R1 is an initial maximum distance threshold. If this initial maximum distance threshold is used to determine whether or not the marker device 1 has rotated about its mount 3, then a rotation of the joint between the two bones 4a and 4b about the joint axis 7 would also be considered to be such an unintentional rotation. This would result in a false positive in the indication information. In this example embodiment, a joint axis indication information dataset is therefore acquired by the CPU 12, for example by indicating the joint axis 7 using a pointer (not shown) which is tracked using the tracking camera 17. The CPU 12 then calculates the distance between the joint axis 7 and the central point 5 of the marker device 1 and adjusts the maximum distance threshold to be below this distance. In this example embodiment, the maximum distance threshold is adjusted to the radius of the circle R2.

In this example embodiment, it is advantageous if the maximum distance threshold is larger than the distance between the mechanical axis 8 of the mount 3 and the central point 5 of the marker device 1. The CPU 12 therefore uses a pointer, which is tracked by the tracking camera 17, to acquire a mechanical axis indication information dataset from which it can calculate the distance between the mechanical axis 8 and the central point 5 in order to set the maximum distance threshold accordingly. For adjusting the maximum distance threshold, the CPU 12 can consider the distance between the central point 5 and the mechanical axis 8, the distance between the central point 5 and the joint axis 7 or both of these in combination.

Figure 3A:
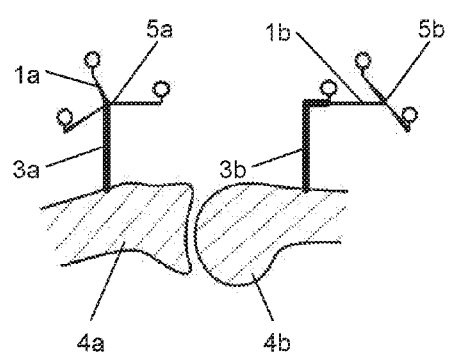
FIGS. 3a and 3b illustrate a configuration comprising two marker devices.
Figure 3B:
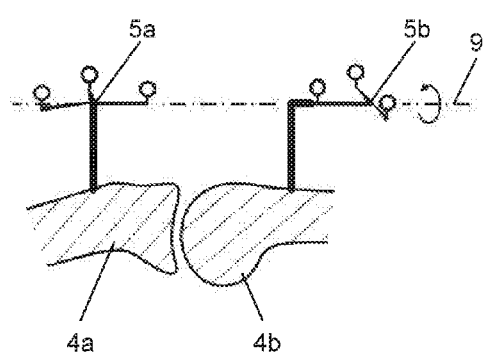

FIGS. 3a and 3b show a configuration comprising two objects, such as for example bones 4a and 4b, wherein each object is provided with a marker device. The marker device 1a is connected to the bone 4a via the mount 3a, while the marker device 1b is connected to the bone 4b via the mount 3b. FIG. 3a shows this configuration in a first rotational position, while FIG. 3b shows this configuration in a second rotational position. The two depicted positions differ in that a rotation has occurred about an axis of rotation 9 which is closer to the central points 5a and 5b of the marker devices 1a and 1b, respectively, than the maximum distance threshold.

The axis of rotation is calculated independently for each marker device 1a, 1b by the CPU 12 in the way explained above. The calculated axis of rotation equals the axis 9 for each marker device 1a, 1b. In normal processing, the CPU 12 would determine an unintentional movement of the marker devices 1a and 1b due to the distance between the axis of rotation 9 and the central points 5a and 5b, respectively. In this embodiment, however, the CPU 12 compares the independently calculated axes of rotation of the two marker devices 1a and 1b and determines that these two axes are identical. In this case, the CPU 12 concludes that the rotations of the marker devices 1a and 1b were not unintentional, because it is unlikely that both marker devices 1a and 1b would have undergone an unintentional rotation about the same or a similar axis of rotation. The CPU 12 thus concludes that the rotation of a marker device was not about its mount 3 if the divergence between the two axes of rotation of two different marker devices is below a predetermined axis divergence threshold. The divergence between the axes describes the distance and/or angle between two axes of rotation.

Figure 5:
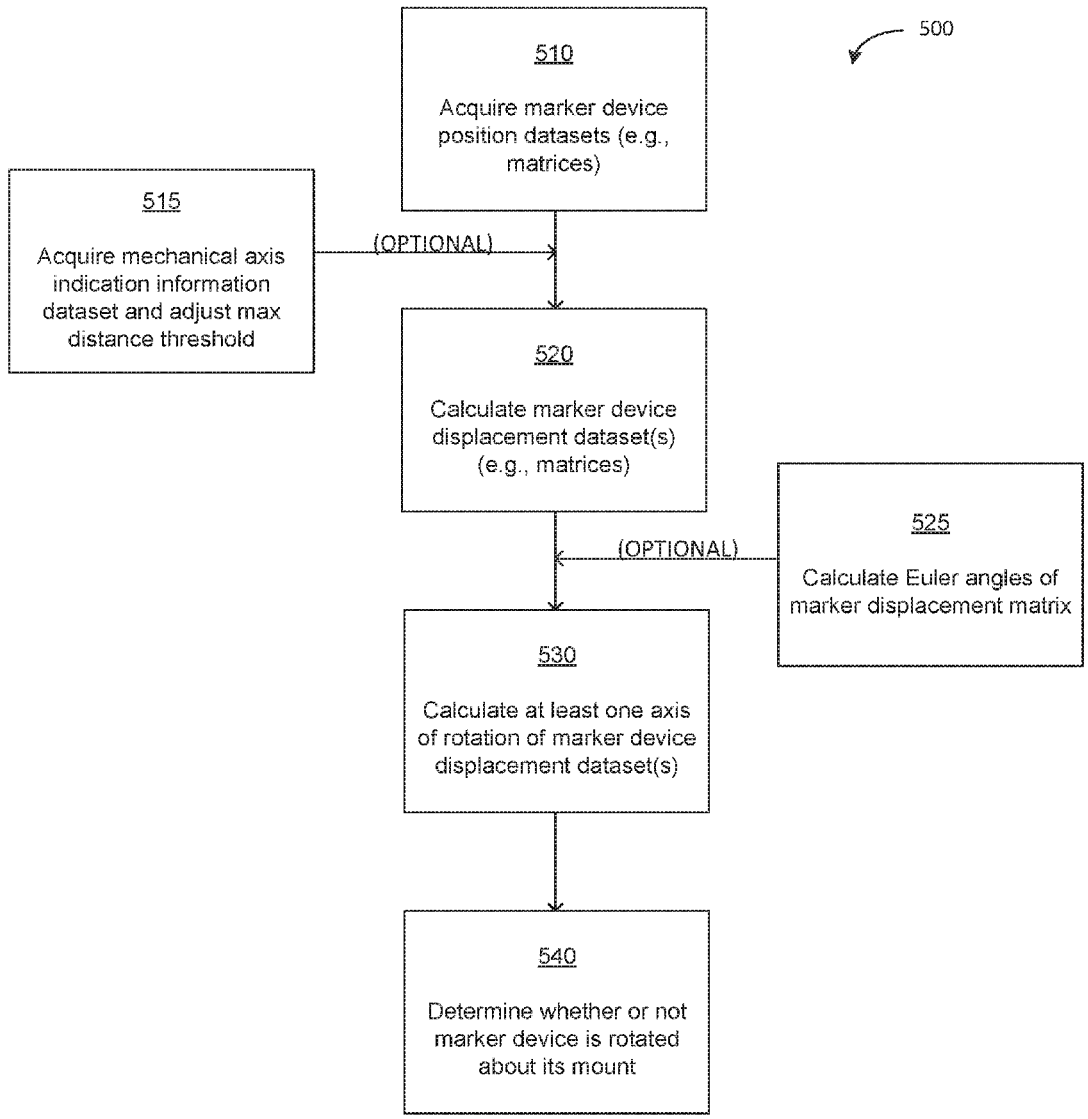
FIG. 5 illustrates an exemplary flow diagram for determining rotation by a marker device of a medical tracking system about its mount.

FIG. 5 illustrates an exemplary flow diagram 500 for determining rotation by a marker device of a medical tracking system about its mount. Beginning at step 510, the step involves acquiring marker device position datasets representing position of the marker device before and after movement. Step 520 involves calculating a marker device displacement dataset which represents the displacement of the marker device. Step 530 involves calculating at least one axis of rotation of the marker device displacement dataset. Step 540 involves determining whether or not the marker device is rotated about its mount from the position of the at least one axis of rotation relative to the marker device. Optionally, step 515 involves acquiring a mechanical axis indication information dataset which represents information on the position of a mechanical axis of the mount and adjusting the maximum distance threshold in accordance with the mechanical indication information dataset. Optionally step 525 involves calculating the Euler angles of a marker device displacement matrix and performing the step of determining the at least one axis of rotation and all subsequent steps only if at least one of the Euler angles is larger than a predetermined minimum angle threshold.

Figure 6A:
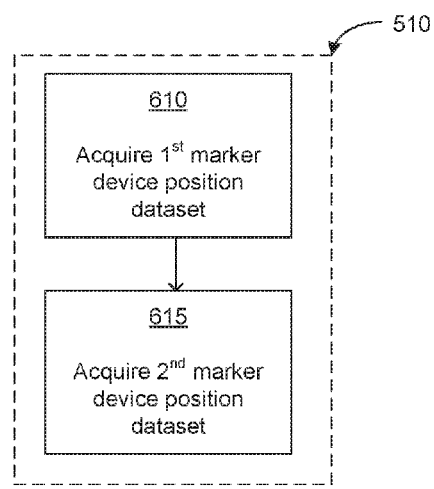
FIG. 6A illustrates an embodiment of the flow diagram of FIG. 5.

FIG. 6A illustrates an embodiment of step 510 of FIG. 5. Beginning at step 610, the step involves acquiring a first marker device position dataset which represents the (first) position of the marker device before a movement of the marker device. Step 615 involves acquiring a second marker device position dataset which represents the (second) position of the marker device after a movement of the marker device.

Figure 6B:
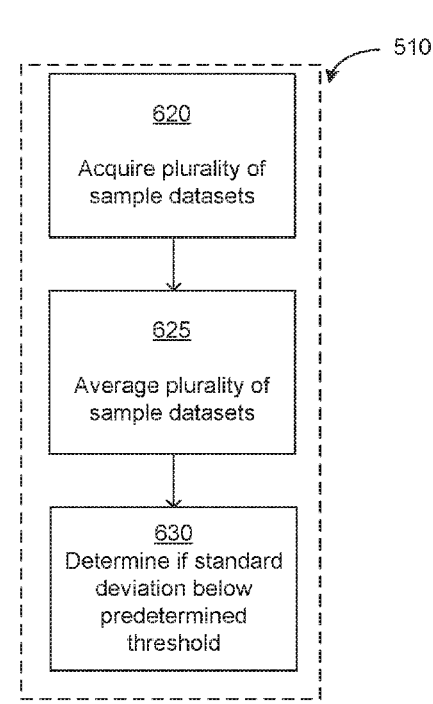
FIG. 6B illustrates an embodiment of the flow diagram of FIG. 5.

FIG. 6B illustrates a further embodiment of step 510 of FIG. 5 in which datasets are averaged. Beginning at step 620, a marker device position dataset is acquired by acquiring a plurality of sample datasets. Step 625 involves averaging the plurality of sample datasets, and step 630 involves determining if the standard deviation of the sample datasets is below a predetermined position threshold. The averaging process eliminates the noise which occurs when ascertaining the position of the marker device using the receiver of the tracking system.

In one example, the marker device position dataset may be acquired by acquiring a plurality of sample marker device position datasets, averaging the plurality of sample marker device position datasets and using the average as the marker device position dataset if the standard deviation of the sample marker device position datasets is below a predetermined position threshold. In another example, the marker device position dataset is acquired by sampling, for each marker of the marker device, a plurality of sample marker position datasets which each represent the position of the respective marker, averaging the plurality of sample marker position datasets and using the average as a marker position in the marker device position dataset if the standard deviation of the sample marker position datasets for each marker is below a predetermined position threshold. This example is similar to the previous example, but instead of averaging the position of the marker device as a whole, the positions of the respective markers of the marker device are averaged.

Figures 7, 8:
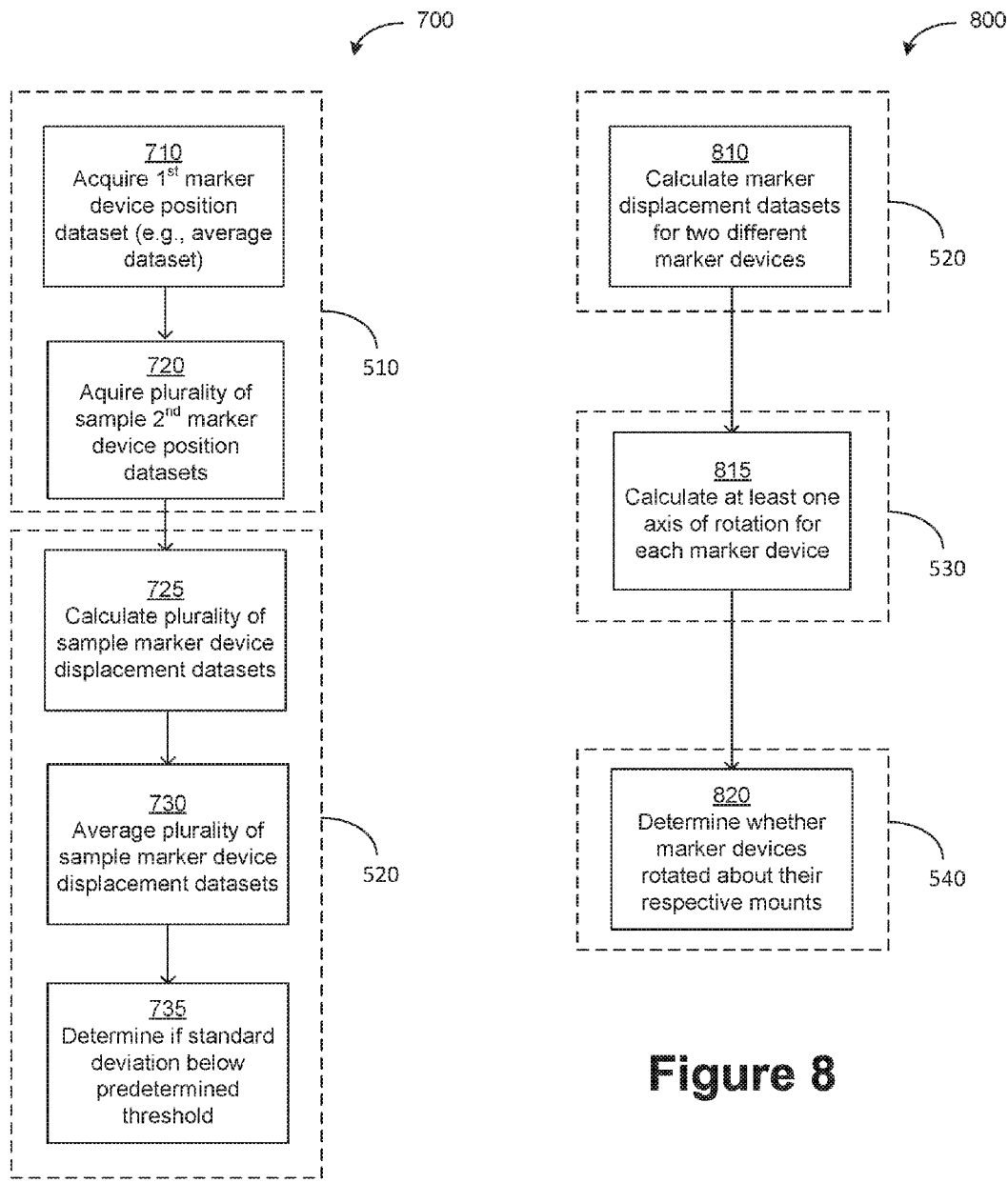
FIG. 7 illustrates an embodiment of the flow diagram of FIG. 5.
FIG. 8 illustrates an embodiment of the flow diagram of FIG. 5.

FIG. 7 illustrates another embodiment 700 of step 510 and step 520 of FIG. 5 using averaging. Beginning at step 710, a first marker device position dataset is acquired, such as an average dataset. At step 720, a plurality of sample second marker device position datasets are acquired. At step 725, a plurality of sample marker device displacement datasets are calculated which each represent the displacement of the marker device between the first marker device position dataset and a corresponding sample second marker device position dataset of the plurality of sample second marker device position datasets. At step 730, the plurality of sample marker device displacement datasets are averaged, and at step 735 a determination is made if the standard deviation of the plurality of sample marker device displacement datasets is below a predetermined displacement threshold.

FIG. 8 illustrates an embodiment 800 of FIG. 5 relating to the presence of two different marker devices, and illustrating embodiments of steps 520, 530, and 540. Beginning at step 810, marker device displacement datasets are calculated for the two different marker devices. At step 815, at least one axis of rotation is calculated for each marker device. This may be performed as described above for a single marker device. At step 820, the determination is made whether the marker devices have rotated about their respective mounts. The marker devices are determined to have not rotated about their respective mounts if each axis of rotation of the first marker device has a corresponding axis of rotation of the second marker device at a distance which is below a predetermined axis divergence threshold.

It should be noted that the present invention relates solely to analysing a movement of a marker device which is attached to an object. The present invention does not encompass the process of attaching the marker device to the object. In addition, the movement of the marker device does not even have to be caused by a movement of the object which the marker device is attached to.

We claim:

1. A method comprising:
   acquiring, by a tracking device, a first position of a marker device, wherein the marker device includes a plurality of markers and a mount, and wherein the plurality of markers are attached via a rigid connection to the mount and the mount is attached to an object;
   using, by a computer operably associated with the tracking device, the first position of the marker device to generate a first marker device position dataset that represents a position of the marker device before a movement of the marker device;
   acquiring, after the movement of the marker device, and by the tracking device, a second position of the marker device;
   using, by the computer, the second position of the marker device to generate a second marker device position dataset that represents the position of the marker device after the movement of the marker device;
   calculating, by the computer, a marker device displacement dataset from the first and the second marker device position datasets, the marker device displacement dataset representing a displacement of the marker device;
   calculating, by the computer, at least one axis of rotation of the displacement of the marker device from the marker device displacement dataset, the calculated at least one axis of rotation including a position of the at least one axis of rotation;
   determining, by the computer, whether the marker device is rotated about the mount due to a rotation of at least part of the mount relative to the object based on the position of the at least one axis of rotation relative to the marker device, the marker device being determined to have rotated about the mount in a condition that a distance between the position of the at least one axis of rotation and a point defined relative to the marker device is below a predetermined maximum distance threshold, the predetermined maximum distance threshold being based on an at least one physical parameter of the marker device; and
   outputting a warning to an associated user in a condition that the computer has determined that the marker device has rotated about the mount, the warning alerting the associated user that the marker device has rotated about the mount.

2. The method according to claim 1, wherein the first and the second marker device position datasets are marker device position matrices, and the marker device displacement dataset is a marker device displacement matrix.

3. The method according to claim 2, further comprising:
   calculating Euler angles of the marker device displacement matrix; and
   calculating the at least one axis of rotation and determining whether or not the marker device is rotated about the mount only if at least one of the Euler angles is larger than a predetermined minimum angle threshold.

4. The method according to claim 2, wherein the at least one axis of rotation is calculated as an eigenvector of the marker device displacement matrix.

5. The method according to claim 4, wherein only one axis of rotation corresponding to the eigenvector with a largest eigenvalue is determined.

6. The method according to claim 2, wherein the marker device displacement matrix is calculated as a product of an inverse of the second marker device position matrix and the first marker device position matrix.

7. The method according to claim 1, further comprising:
   acquiring a mechanical axis dataset that represents information on a position of a mechanical axis of the mount; and
   adjusting the predetermined maximum distance threshold in accordance with the mechanical axis dataset.

8. The method of claim 7, wherein the predetermined maximum distance threshold is a predetermined percentage larger than the distance between a reference point of the marker device and the mechanical axis of the mount.

9. The method of claim 8, wherein the predetermined percentage is between 2% and 25%.

10. The method according to claim 1, wherein the marker device is determined to have rotated about the mount if a difference between a determined axis of rotation and a mechanical axis of the mount is below a predetermined axis deviation threshold.

11. The method according to claim 1, wherein a marker device position dataset is acquired by acquiring a plurality of sample marker device position datasets, averaging the plurality of sample marker device position datasets and using the average as the marker device position dataset in a condition that a standard deviation of the sample marker device position datasets is below a predetermined position threshold.

12. The method according to claim 1, wherein a marker device position dataset is acquired by sampling, for each marker of the marker device, a plurality of sample marker position datasets that each represent a position of the respective marker, averaging the plurality of sample marker position datasets and using the average as a marker position in the marker device position dataset in a condition that a standard deviation of the sample marker position datasets for each marker is below a predetermined position threshold.

13. The method according to claim 1, wherein:
   a plurality of sample second marker device position datasets are acquired, each sample second marker device position dataset representing a sampled set of second marker device position data;

a plurality of sample marker device displacement datasets are calculated, which each represent the displacement of the marker device between the first marker device position dataset and a corresponding sample second marker device position dataset of the plurality of sample second marker device position datasets;

the plurality of sample marker device displacement datasets are averaged; and the average of the plurality of sample marker device displacement datasets is used as the marker device displacement dataset in a condition that a standard deviation of the plurality of sample marker device displacement datasets is below a predetermined displacement threshold.

14. The method according to claim 1, wherein:

marker device displacement datasets are calculated for two different marker devices, each marker device having a respective mount;

at least one axis of rotation is calculated for each marker device; and the marker devices are determined to have not rotated about their respective mounts in a condition that for each axis of rotation of the first marker device a corresponding axis of rotation of the second marker device is at a distance which is below a predetermined axis divergence threshold.

15. The method of claim 1, wherein the rigid connection comprises lockable axes of rotation.

16. The method of claim 1, wherein the at least one physical parameter of the marker device is the size of the marker device or the type of mount.

17. A non-transitory computer readable storage device storing a computer program which, when running on a computer or when loaded onto the computer, causes the computer to:

acquire, via a tracking device operably associated with the computer, a first position of a marker device, wherein the marker device includes a plurality of markers and a mount, and wherein the plurality of markers are attached via a rigid connection to the mount and the mount is attached to an object;

use, by the computer, the first position of the marker device to generate a first marker device position dataset that represents a position of the marker device before a movement of the marker device;

acquire, after the movement of the marker device, and by the tracking device, a second position of the marker device;

use, by the computer, the second position of the marker device to generate a second marker device position dataset that represents the position of the marker device after the movement of the marker device;

calculate a marker device displacement dataset from the first and second marker device position datasets, the marker device displacement dataset representing a displacement of the marker device;

calculate at least one axis of rotation of the displacement of the marker device from the marker device displacement dataset, the calculated at least one axis of rotation including a position of the at least one axis of rotation;

determine whether the marker device is rotated about the mount due to a rotation of at least part of the mount relative to the object based on the position of the at least one axis of rotation relative to the marker device, the marker device being determined to have rotated about the mount in a condition that a distance between the position of the at least one axis of rotation and a point defined relative to the marker device is below a predetermined maximum distance threshold, the predetermined maximum distance threshold being based on an at least one physical parameter of the marker device; and output a warning to an associated user in a condition that the computer has determined that the marker device has rotated about the mount, the warning alerting the associated user that the marker device has rotated about the mount.

18. The non-transitory computer readable storage device of claim 17, wherein the rigid connection comprises lockable axes of rotation.

19. A method comprising:

acquiring, by a tracking device, a first position of a marker device, wherein the marker device includes a plurality of markers and a mount, and wherein the plurality of markers are attached via a rigid connection to the mount and the mount is attached to an object;

using, by a computer operably associated with the tracking device, the first position of the marker device to generate a first marker device position dataset that represents a position of the marker device before a movement of the marker device;

acquiring, after the movement of the marker device, and by the tracking device, a second position of the marker device;

using, by the computer, the second position of the marker device to generate a second marker device position dataset that represents the position of the marker device after the movement of the marker device;

calculating, by the computer, a marker device displacement matrix from the first and the second marker device position datasets, the marker device displacement matrix representing a displacement of the marker device;

calculating, by the computer, Euler angles of the marker device displacement matrix;

determining, by the computer, that at least one of the Euler angles is larger than a predetermined minimum angle threshold;

calculating, by the computer, at least one axis of rotation of the displacement of the marker device from the marker device displacement matrix, the calculated at least one axis of rotation including a position of the at least one axis of rotation;

determining, by the computer, whether the marker device is rotated about the mount due to a rotation of at least part of the mount relative to the object based on the position of the at least one axis of rotation relative to the marker device, the marker device being determined to have rotated about the mount in a condition that a distance between the position of the at least one axis of rotation and a point defined relative to the marker device is below a predetermined maximum distance threshold, the predetermined maximum distance threshold being based on an at least one physical parameter of the marker device; and outputting a warning to an associated user in a condition that the computer has determined that the marker device has rotated about the mount, the warning alerting the associated user that the marker device has rotated about the mount.

20. The method of claim 19, wherein the rigid connection comprises lockable axes of rotation.

* * * * *